United States Patent
Fraden et al.

(10) Patent No.: US 6,773,405 B2
(45) Date of Patent: Aug. 10, 2004

(54) EAR TEMPERATURE MONITOR AND METHOD OF TEMPERATURE MEASUREMENT

(76) Inventors: Jacob Fraden, 2611 Hidden Valley Rd., La Jolla, CA (US) 92037; Richard K. Ferlito, 4380 Calle Mejillones, San Diego, CA (US) 92130

(*) Notice: Subject to any disclaimer, the term of this patent is extended or adjusted under 35 U.S.C. 154(b) by 0 days.

(21) Appl. No.: 09/927,179

(22) Filed: Aug. 8, 2001

(65) Prior Publication Data

US 2002/0035340 A1 Mar. 21, 2002

Related U.S. Application Data

(60) Provisional application No. 60/233,104, filed on Sep. 15, 2000.

(51) Int. Cl.[7] ................................................ A61B 5/00
(52) U.S. Cl. ..................................................... 600/549
(58) Field of Search ................................ 600/474, 549, 600/379; 374/100

(56) References Cited

U.S. PATENT DOCUMENTS

| | | | | |
|---|---|---|---|---|
| 3,156,117 A | * | 11/1964 | Benzinger | 600/549 |
| 3,531,992 A | * | 10/1970 | Moore | 600/549 |
| 4,183,248 A | * | 1/1980 | West | 374/164 |
| 4,651,750 A | * | 3/1987 | Northeved | 600/549 |
| 4,880,076 A | * | 11/1989 | Ahlberg et al. | 181/130 |
| 5,062,432 A | * | 11/1991 | James et al. | 600/549 |
| 5,333,622 A | * | 8/1994 | Casali et al. | 128/864 |
| 5,673,692 A | * | 10/1997 | Schulze et al. | 600/301 |
| 6,179,785 B1 | * | 1/2001 | Martinosky et al. | 600/549 |
| 6,283,915 B1 | * | 9/2001 | Aceti et al. | 600/300 |
| 6,450,970 B1 | * | 9/2002 | Mahler et al. | 600/549 |
| 6,556,852 B1 | * | 4/2003 | Schulze et al. | 600/323 |
| 2001/0025151 A1 | * | 9/2001 | Kimball et al. | 600/593 |
| 2002/0010390 A1 | * | 1/2002 | Guice et al. | 600/300 |
| 2002/0114375 A1 | * | 8/2002 | Pompei | 374/133 |
| 2002/0138017 A1 | * | 9/2002 | Bui et al. | 600/537 |
| 2003/0139686 A1 | * | 7/2003 | Rubinstein | 600/549 |

FOREIGN PATENT DOCUMENTS

CH 514 834 C2 * 4/2001 ............. H02J/7/00

* cited by examiner

Primary Examiner—Mary Beth Jones
Assistant Examiner—Jonathan Foreman (57) ABSTRACT

A continuous body core temperature monitor comprises a pliable ear plug that conforms to the shape of an ear canal and incorporates a temperature sensor that is clamped between the plug and the ear canal wall. The external surface of the plug is connected to an external temperature sensor and a heating element that compensate for a heat lost from the ear canal to the environment by maintaining the temperature gradient between the temperature sensor and the heating element close to zero.

11 Claims, 6 Drawing Sheets

EAR TEMPERATURE MONITOR AND METHOD OF TEMPERATURE MEASUREMENT

This application claims the benefit of Provisional application No. 60/233,104 filed Sep. 15, 2000.

FIELD OF THE INVENTION

This invention relates to a method of monitoring temperature of a human body and devices for achieving same and, more particularly, to such a method and device which monitors the internal core temperature of a person undergoing continuous medical observation.

DESCRIPTION OF PRIOR ART

Frequently, during surgical and other medical procedures related to humans and animals, there is a need for continuous monitoring of the body core temperature. Core temperature here means temperature of blood flowing around the brain and other vital internal organs. It has been recognized long time ago that the core temperature is an accurate parameter for assessing the physiological functions and metabolic activity of a body.

Traditionally, there are several known devices for continuous assessing body temperature of a patient. All these devices primarily differ by the measurement site. Specifically, they are 1) an esophageal probe, 2) a rectal probe, 3) skin temperature probes, and 4) an intermittent instant ear thermometers, often called tympanic. The last device presently can not provide a continuous monitoring. The first two devices yield accuracy well acceptable for the diagnostic and monitoring purposes and account for the majority of present temperature recordings. These traditional devices are invasive, may require sterile probes (esophageal), often inconvenient and, as a rule, not acceptable for patients outside the operating rooms. A skin temperature monitoring is used sporadically as it is more influenced by the ambient temperature. The need for an easy, inexpensive, accurate, and comfortable way of continuous temperature monitoring is substantial.

It has been recognized long time ago that the tympanic region of the ear canal follows the body core temperature with high fidelity. The region includes the tympanic membrane and the adjacent walls of the ear canal. This premise has been the basis for the tympanic thermometers, including both the contact and non-contact (infrared) types. An example of a contact transducer is a miniature thermistor (produced, for example, by Vital Signs, Inc.) that is positioned directly on the surface of a tympanic membrane with the connecting wires secured inside the ear canal. Generally, this can be performed only on an anesthetized patient with a risk of damaging the tympanic membrane and thus is rarely used in medical practice. Another example is a contact temperature transducer that is incorporated into an ear plug (U.S. Pat. No. 3,274,994). Examples of continuous noncontact optical infrared probes are given in U.S. Pat. Nos. 3,282,106 and 3,581,570.

Contact detectors are much simpler than noncontact, but they both suffer from the same effect—difficulty of a reliable placement inside the ear canal. Placement of a contact temperature transducer inside the ear canal without a reliable securing of it at any specific position may cause a high inaccuracy in measurement, due to unpredictable effects of the ambient temperature and placement technique of the probe. An attempt to incorporate a temperature transducer into an ear plug similar to a hearing aid device is exemplified by U.S. Pat. No. 5,333,622 issued to Casali, et al. Yet, the teaching does not resolve the accuracy problem due to heat loss. Besides, such a probe requires an individual tailoring of its shape. It should be noted that besides a temperature measurement, there are some other types of measurements that may require a secure adaptive positioning of a transducer inside a body cavity.

Therefore, it is a goal of this invention to produce a sensing device that can be positioned securely and reliably in a body cavity;

Another goal of the invention is to make an ear temperature transducer with a contact probe that is automatically secured at an ear canal wall;

It is another goal of this invention to produce an ear temperature transducer that tracks the core temperature with high fidelity;

It is another goal of this invention to make an ear temperature transducer that is less influenced by the ambient temperature;

It is another goal to provide an ear temperature transducer that doesn't cause a discomfort for a patient and can remain in the ear canal for a prolonged time;

SUMMARY OF THE INVENTION

The goals of this invention is achieved by the novel ear temperature detector. The detector is comprised of an ear plug carrying the temperature sensing device wherein the sensing device is characterized by its increased thermal coupling to a wall of an ear canal and decreased coupling to the environment. This is attained by pre-shaping the plug into a smaller size and allowing to change its shape upon the insertion, until the sensing device is clamped between the plug and the skin. To correct for a thermal gradient across the ear plug, the plug has low thermal conductivity and its external temperature is monitored. Alternatively, temperature of the external portion of the plug is actively controlled by a heater attached to the plug. The heater forms a thermal shield around the temperature sensing device, thus negating a thermal gradient across the plug.

DESCRIPTION OF THE PREFERRED EMBODIMENTS

The present invention describes a device and method for obtaining information from a body cavity. At least three essential elements are required for this invention to work: a temperature transducer, a thermal insulator, and an external temperature sensor.

Figure 1:
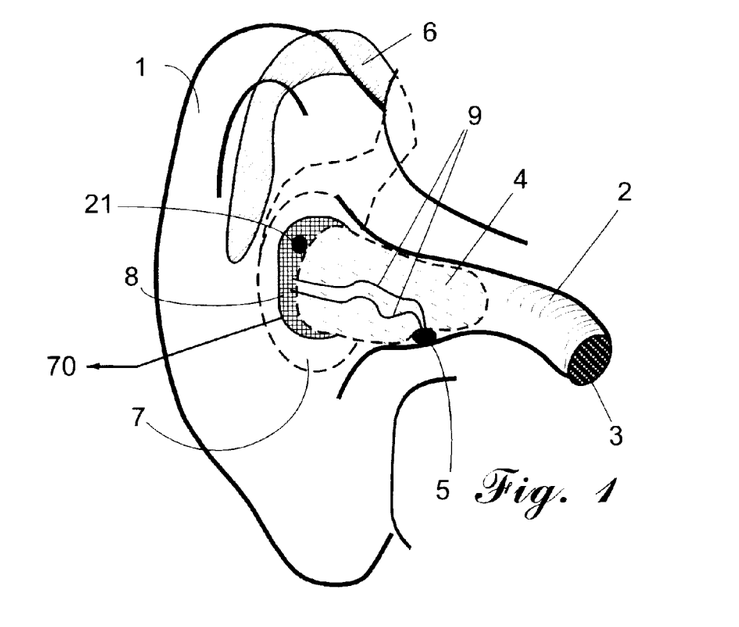
FIG. 1 shows a temperature detector inserted into an ear and secured on a helix.

A preferred embodiment is illustrated herewith by showing how this can be accomplished with improved accuracy when the information is temperature and the body cavity is an ear canal of a human or other animal. The major task for accomplishing the stated goals is to increase a thermal coupling between the ear canal walls and a temperature transducer, while minimizing such coupling to the external environment. FIG. 1 illustrates an ear plug 4 that is inserted into ear 1, but not reaching the tympanic membrane 3. Temperature transducer 5 is clamped between plug 4 and ear canal walls 2. The transducer is connected to the electronic module 8 via wires 9. There may be more than one transducer attached to the plug, but for the preferred embodiment just one is a sufficient example. The module is positioned in the external supporting disk 7 that contains external temperature sensor 21. The entire assembly may be secured on ear 1 by carrier clamp 6 that has shape suitable for encircling the helix of an ear. Naturally, other conventional methods of securing may work as well. Since the ear canal wall temperature is close to that of tympanic membrane 3, it is assumed that transducer 5 can monitor the tympanic temperature, unless plug 4 and wires 9 sink a significant portion of thermal energy from the transducer, resulting in erroneous temperature measurement. The position of transducer 5 inside the ear canal has to be consistent and always between plug 4 and walls 2. The output signal is measured via conductors 70.

Figure 2:
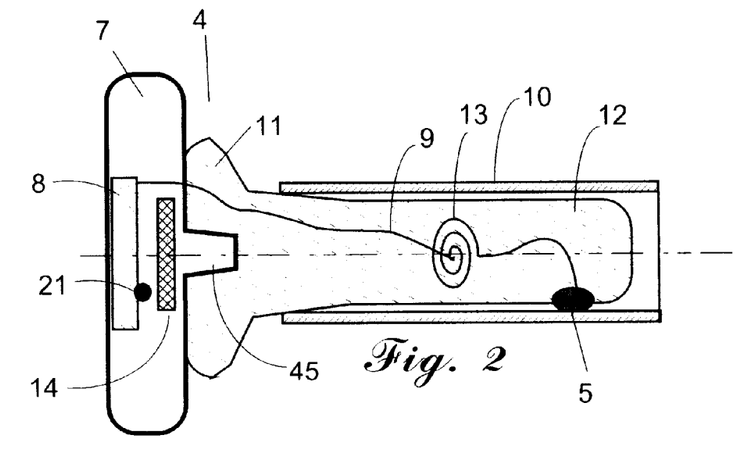
FIG. 2 is a cross-sectional view of an ear temperature detector in a storage state.

To achieve the desired results, transducer 5 is attached to a specific portion of plug 4. That portion preferably should be at the distal end of the plug that would be inserted into a body cavity, such as an ear canal. FIG. 2 shows plug 4 in a storage stage, that is, before it is inserted into an ear. The plug has two ends—base 11 and tip 12. The base is attached to an external enclosure. The enclosure is in form of disk 7 that may have a protruding pin 45 inside the plug for better mechanical and thermal coupling between disk 7 and plug 4. In a storage state or just prior the insertion into the ear canal, tip 12 is compressed to a size that is smaller than the inner dimension of the ear canal. To retain such reduced shape for a long time, the tip may be inserted into storage sleeve 10 that provides a constraining compression. The sleeve may be a plastic tube. Plug 4 is fabricated of pliable material that may be collapsed when squashed (compressed) and recover its original shape (expand) when external pressure is released. The plug serves as a thermal insulator. Its thermal conductivity should be minimal, thus foams are the best choice of the material. An example of such a material is water-born hydrophilic foam. The foam should not have a significant dimensional memory so that it returns to the original expanded shape after prolonged storage in the collapsed (compressed) shape.

For a better thermal speed response, temperature transducer 5 is secured on the surface of tip 12. The transducer should have a small size and may be of any suitable design—thermistor, thermocouple, semiconductor, etc. Wires 9 should sink out as little heat as possible, thus they need to be fabricated as thin as practical and should have an extended length inside or on the surface of plug 4. To increase the length, wires 9 may be formed into loop 13 that is positioned between transducer 5 and electronic module 8, regardless of position of the module (explained below).

Before insertion of the plug into an ear canal, sleeve 10 is removed and discarded. Shape of tip 12 slowly returns to that which was prefabricated before the installation of sleeve 10. Alternatively, tip 12 may be squashed by an operator just before the insertion. The rate of the shape recovery should be sufficiently slow to allow enough time for the insertion of plug 4 into an ear canal. Practically, the shape recovery time should be greater than 3 seconds. After the collapsed tip 12 is inserted into an ear canal, its continuous shape recovery forces plug 4 to conform with the shape of an ear canal. The expansion of plug 4 stops when it completely fills up the adjacent ear canal volume. This allows transducer 5 to be forcibly compressed against ear canal wall 2, while still being electrically connected to electronic module 8 via wires 9, as shown in FIG. 1.

Figure 4:
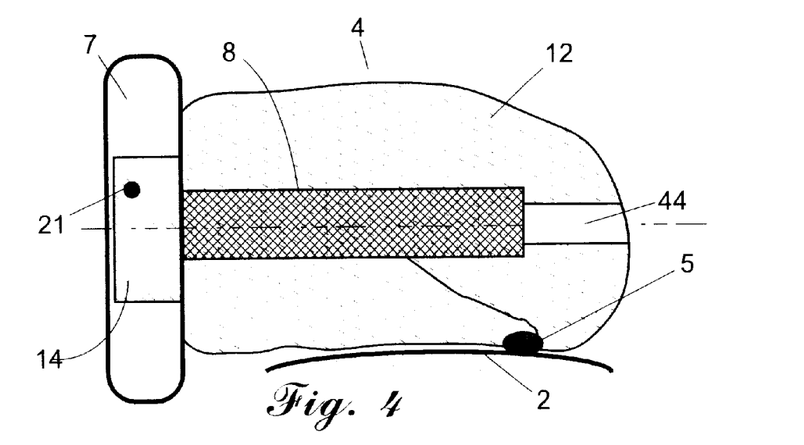
FIG. 4 is a temperature detector with the electronic module inside the plug.

Electronic module 8 may contain the amplifier, power supply, signal conditioner, transmitter and other components, or it may be a simple connecting device. In some embodiments, module 8 may be positioned directly inside plug 4 as shown in FIG. 4. In this case the size of module 48 should be small enough to allow compression of tip 12 before the insertion. Module 8 may be used for many other purposes, in addition to or instead of measuring temperature. An example is generating sound. In that case, opening 44 in plug 4 may be required for better sound coupling to the tympanic membrane.

It should be stressed that an ear canal is just an example of an application and the identical concept of an expandable plug with an attached transducer can be used for producing an insert for other body cavities, for example, nasal. Further, there maybe other than temperature transducers attached to the plug, for example acoustic.

Figure 5:
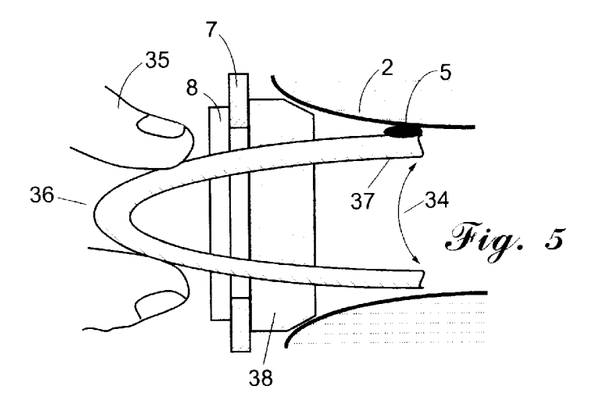
FIG. 5 is a fork version of an ear plug.

Another possible embodiment of plug 4 is shown in FIG. 5 where the plug is made in shape of flexible fork 36 having a spring action. The end of the fork is squeezed by fingers 35 before the insertion and let go after. The fork has arm 37 that carries transducer 5. After the fork is released, it expands so that its arm 37 compresses transducer 5 against ear canal wall 2. To improve thermal separation of transducer 5 from the outside, the fork may be supplied with insulator 38. Other components, like the wires, the loop, the electronic module, etc, are not shown in FIG. 5.

Figure 3:
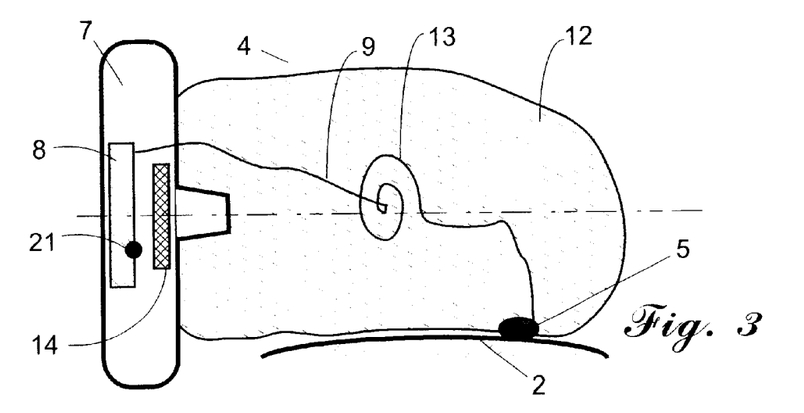
FIG. 3 is a cross-sectional view of a temperature detector in expanded state.
Figure 6:
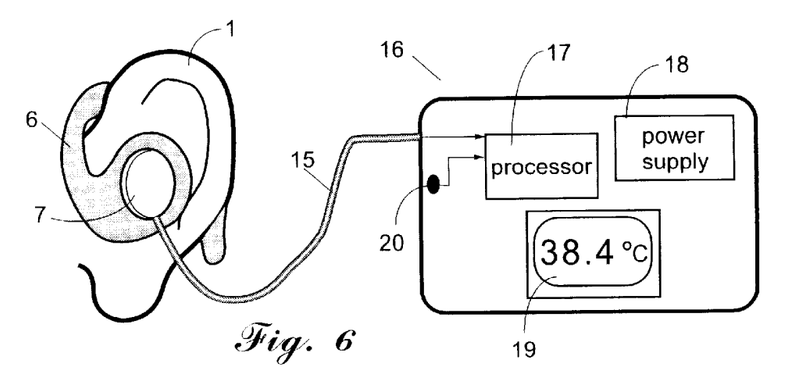
FIG. 6 shows a block diagram of a temperature monitor.
Figure 7:
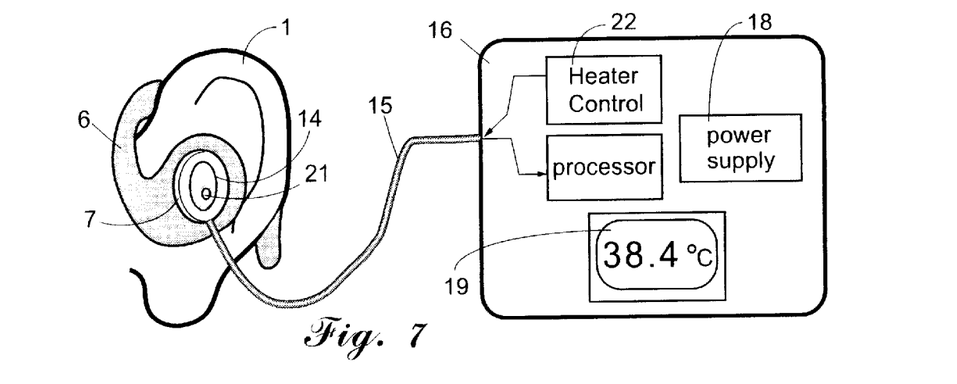
FIG. 7 depicts a block diagram of a temperature monitor with an additional heater.

The expanded plug 4 performs an important function—positioning and clamping transducer 5 on an ear canal wall surface. The other critical function—minimizing effects of the ambient temperature may be accomplished by at least two methods. One method is a mathematical correction and the other is an active compensation. The method of a mathematical correction of an error is performed by the use of an additional ambient temperature sensor that is positioned either directly on disk 7 as external sensor 21 (FIGS. 2 and 3), or in/on the external monitor 16 as ambient sensor 20 (FIG. 6). Note that for this method, heater 14 is not required and only one sensing device—either ambient sensor 20 or external sensor 21 is needed. Disk 7 of an ear device is connected to monitor 16 via cable 15 (FIGS. 6 and 7). Monitor 16 may contain signal processor 17, power supply 18, display 19 and other components. Ambient sensor's 20 or external sensor's 21 signal is processed and used to correct for errors in the ear temperature measurement. The degree of correction needs to be established experimentally for a particular plug design. The corrected body temperature $t_b$ may be determined through a temperature gradient, for example, as:

$$t_b = t_s + \mu(t_s - t_a) \quad (1)$$

where $\mu$ is the experimental constant, $t_a$ is the temperature measured by ambient sensor 20 or external sensor 21 and $t_s$ is the reading of ear temperature transducer 5.

The above method of error correction, however, has it's limitations. One is the uncertainty in the value of constant $\mu$. Another limitation is the use of ambient sensor 20. Having ambient sensor 20 placed at monitor 16, makes the mathematical correction less effective when, for example, the patient is laying on the ear which is being monitored and thus having the external ear temperature significantly different from that of ambient monitored by sensor 20.

A more effective method of the error reduction is an active heat loss compensation that is shown in FIG. 7. It is based on forming a thermal shield around temperature transducer 5. Disk 7 carries heater 14 and external temperature sensor 21, positioned on or near heater 14 with a good thermal coupling between them. Note that disk 7 is located outside of the ear canal, directly at it's opening. Heater 14 also may be seeing in FIGS. 2, 3 and 4. The heater controller, that is positioned either inside disk 7 or in monitor 16, as shown in FIG. 7, receives signal from external sensor 21 and controls temperature of heater 14 to a required level, that should be close to the actual body temperature as monitored by transducer 5. Thus, heater 14 minimizes temperature gradient between temperature transducer 5 and heater 14. It acts as a thermal shield between temperature transducer 5 and the environment. Circuit diagram of FIG. 8 further illustrates this method. A reference point for the heater control is provided by temperature transducer 5 positioned inside the ear canal and compressed by plug 4 to the ear canal wall. Both temperature transducer 5 and external sensor 21 are connected to the Wheatstone bridge circuit with two pull-up resistors 30 and 31. Thermal coupling between transducer 5 and the ear canal walls needs to be much better than between temperature transducer 5 and the external components, that is, external sensor 21 and heater 14. This is primarily accomplished by the use of thermally insulating plug 4. An excessive thermal coupling between temperature transducer 5 and external sensor 21 may result in undesirable instability of the control circuit. Error amplifier 32 compares the output signals from temperature transducer 5 and external sensor 21 and controls heater controller 22, that in turn, via conductors 33, adjusts electric power to heater 14. This circuit maintains temperature of heater 14 close to that of temperature transducer 5. This results in a negligible heat transfer through plug 4 and elimination of the error in temperature measured by temperature transducer 5. Turning again to Eq. 1, we can see that with the active heating of the above thermal shield method, temperatures at both sides of plug 4 equalize: $t_a \approx t_s$ and thus value of $\mu$ become irrelevant, so that $t_b = t_s$. In other words, transducer 5 now directly measures temperature of the body with no influence of the ambient temperature.

Figure 8:
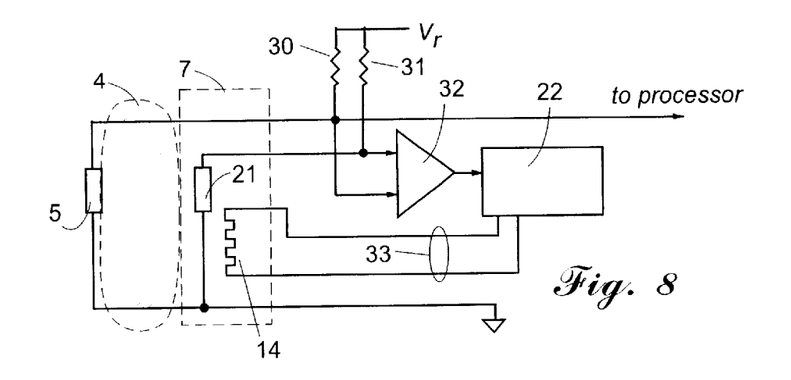
FIG. 8 is an electrical circuit diagram of a controlled heater with thermistor sensors.
Figure 13:
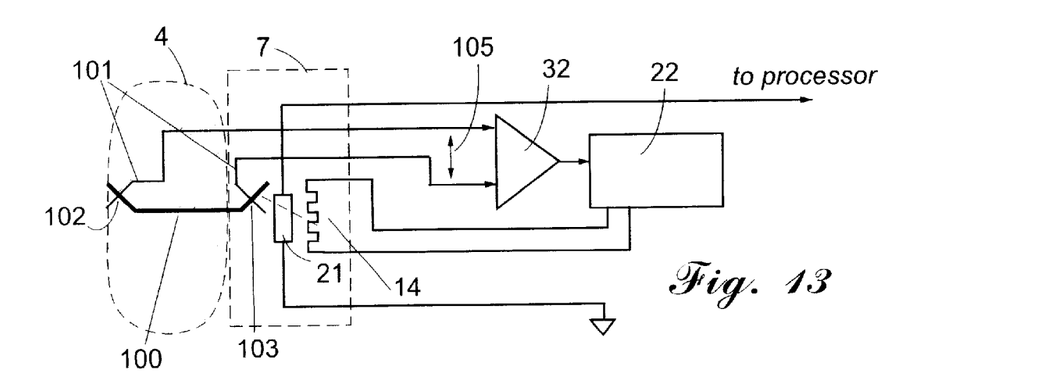
FIG. 13 is an electrical circuit diagram of a controlled heater with a thermocouple sensor.

As a variant of FIG. 8, FIG. 13 illustrates use of a thermocouple temperature transducer having two dissimilar conductors 100 and 101. A thermocouple has two junctions, hot junction 102 and cold junction 103. Hot junction 102 is positioned inside the body cavity at one end of plug 4, while cold junction 103 is thermally attached to heater 14 and external sensor 21 near the other end of plug 4. Heater controller 22 receives signal from thermocouple amplifier 32 and operates such as to bring thermocouple output voltage 105 close to zero. This will establish a minimal thermal gradient across plug 4 so that external sensor 21 indicates the internal body temperature.

Figure 9:
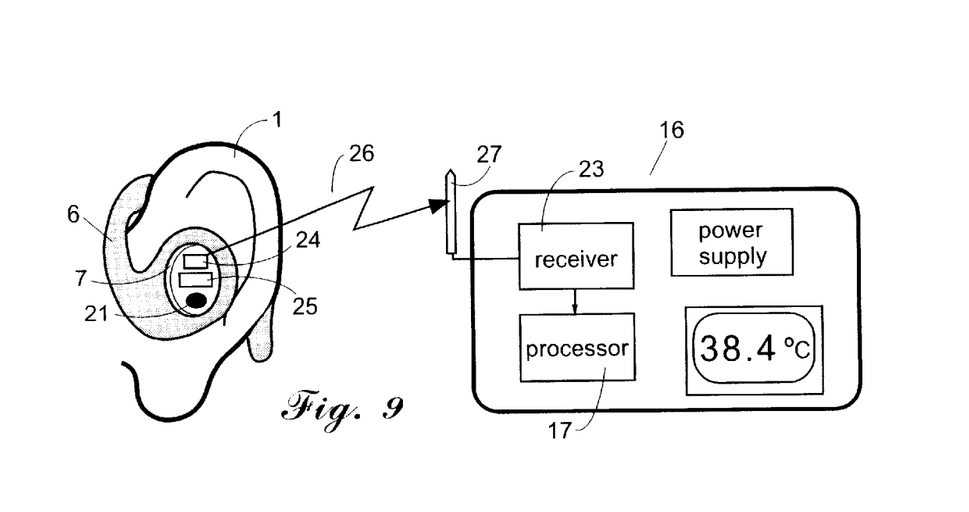
FIG. 9 is a radio telemetry version of a temperature monitor.

The use of cable 15 as shown in FIGS. 6 and 7 may be not desirable, as it may restrict movement of a patient. The cable can be eliminated if disk 7 carries transmitter 24 and power source 25, as illustrated in FIG. 9. Accordingly, monitor 16 needs to contain antenna 27 and receiver 23. The link between the patient and the monitor may be via radio waves 26, or optical (both involve electromagnetic radiation). Alternatively, transmitter 24 and/or power source 25 can be located outside of disk 7, but in that case, an intermediate packaging for these components (not shown) would be required. It should be noted, that in the wireless communication with the monitor, method of a passive error correction is preferable, so that transmitter 24 will send information concerning both transducer 5 and external sensor 21.

Figure 10:
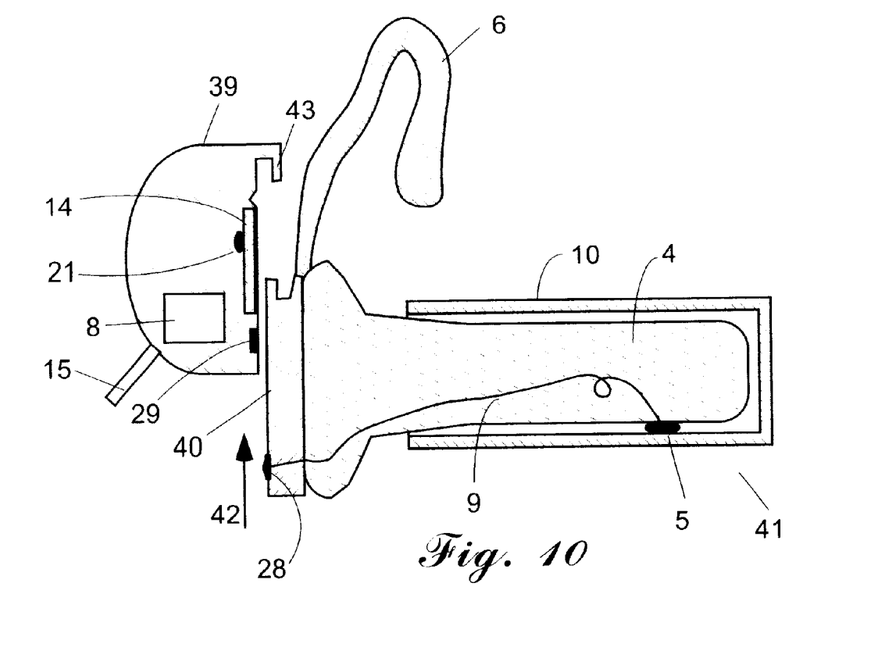
FIG. 10 depicts a practical assembly of an ear temperature detector.

A practical way to produce an ear temperature monitoring device with a thermal shield is shown in FIG. 10. Reusable cup 39 may contain electronic module 8, cable 15, second contacts 29, heater 14, and external sensor 21. A detachable part is disposable insert 41 that contains plate 40, plug 4, and transducer 5 attached via wires 9 to first contacts 28. Before operation, insert 41 is moved in direction 42 to mate with cup 39. Both cup 39 and insert 41 are engaged and retained together during the temperature monitoring with the help of lock 43. Contacts 28 and 29 provide connection between wires 9 and electronic module 8. After the monitoring in completed, disposable insert 41 may be detached from cup 39 and discarded.

Other Embodiments

Figure 11:
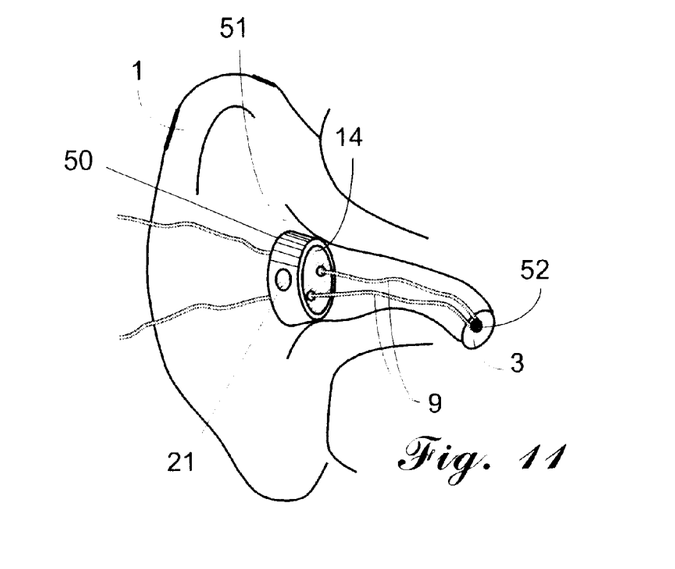
FIG. 11 shows a tympanic sensor with a compensating heater.

A thermal shield method similar to one shown in the preferred embodiment can be employed to reduce effects of the environment with other types of the medical temperature sensors. The general operating principle is basically the same as described above. FIG. 11 shows an example of a temperature transducer 52 that is directly attached to tympanic membrane 3 of ear 1. This embodiment does not necessarily require an expanding plug 4 that has been shown in the prior illustrations. Wires 9 pass through or near heating insert 50 that is inserted into ear opening 51. The heating insert contains external sensor 21 and thermally attached to it heater 14, whose temperature is controlled to approach that measured by transducer 52. As above, wires should be as thin as practical and heater 14 should be thermally de-coupled from transducer 52. Since the thermal gradient across wires 9 between transducer 52 and external sensor 21 becomes small, effects of the ambient temperature also become small, while the accuracy of measurement improves.

Figure 12:
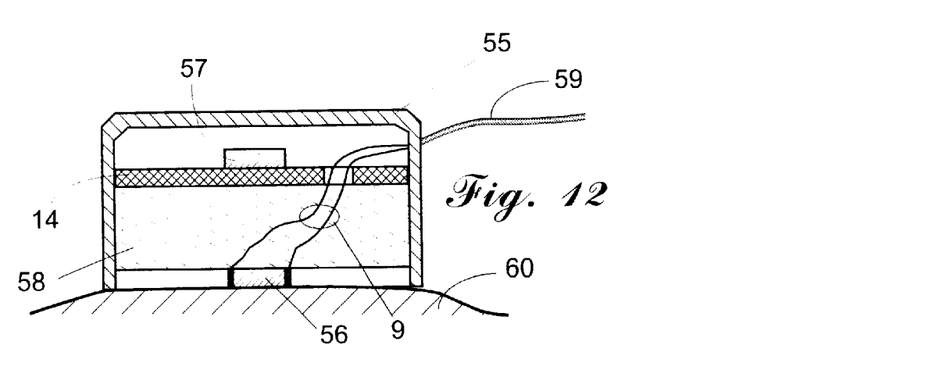
FIG. 12 illustrates a cross-sectional view of a surface temperature sensor.

Another embodiment of the same thermal shield method is depicted in FIG. 12. This is a surface temperature measuring device that can measure a "deep" (subcutaneous) body temperature. The device is comprised of housing 55, skin temperature sensor 56, heater 14, thermal insulator 58, second temperature sensor 57, wires 9, and cable 59. Note that wires 9 pass through insulator 58 and through or near heater 14. Insulator 58 can be a body of polymer foam or even an air gap. In operation, the temperature of second temperature sensor 57 is controlled to approach that of skin temperature sensor 56, by providing thermal energy to heater 14. This forms a thermal shield above skin temperature sensor 57 and minimizes heat loss from skin 60 and, subsequently, to an improved accuracy in temperature measurement. In most practical cases, for an acceptable accuracy, a typical temperature difference between sensors 56 and 57 should be no greater than 2 degrees C. and preferably equal to zero.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

What is claimed is:

1. A temperature sensing device for monitoring an internal temperature of a human or other animal, comprising:
   a flexible member having a spring action such that said flexible member expands after insertion into a body cavity of the animal, said flexible member having an outer surface,
   a temperature transducer coupled to said outer surface, said temperature transducer configured to be in thermal contact with a surface of the body cavity of the animal and operable to measure a surface temperature of the surface of the body cavity,
   a temperature sensor mounted on said outer surface of said flexible member and operative to measure a reference temperature, said temperature sensor being thermally insulated from said temperature transducer by said flexible member and positioned so as to be external to the body cavity after insertion into the body cavity, and
   an electronic module coupled to said temperature transducer and said temperature sensor, said electronic module operable to compute the internal temperature of the animal from the surface temperature and the reference temperature.

2. The device of claim 1, wherein said flexible member further comprises an enclosure and the device further comprises a heater housed in said enclosure, said heater thermally coupled to said temperature sensor and electrically coupled to said electronic module.

3. The device of claim 1, wherein said flexible member is formed in a generally cylindrical shape prior to insertion into the body cavity.

4. The device of claim 1, wherein said flexible member is formed of a compressible material which is capable of collapsing upon application of external pressure and expanding upon release of the external pressure.

5. The device of claim 4, further comprising a retainer that maintains said compressible material in a collapsed state prior to insertion of said flexible member in the body cavity, and which may be removed to allow said compressible material to expand within the body cavity.

6. The device of claim 1, wherein said electronic module further comprises a data transmitter operable to transmit signals associated with temperature measurements of said temperature transducer and said temperature sensor.

7. The device of claim 6, further comprising a monitor coupled to said data transmitter, said monitor including a power supply coupled with a processor configured to use the signals to compute the internal body temperature of the animal.

8. The device of claim 1 wherein said temperature transducer is positioned between the surface of the body cavity and the flexible member.

9. A method of continuously monitoring the internal temperature of a human or other animal, comprising:
   carrying a temperature transducer on an outer surface of a compressible plug,
   compressing the plug,
   inserting the plug into a body cavity of the animal,
   allowing the plug to expand to conform to the shape of the body cavity so as to place the temperature transducer in thermal contact with a body surface of the body cavity,
   measuring the temperature of the body surface with the temperature transducer,
   thermally insulating the temperature transducer from a heater which is thermally coupled with a temperature sensor positioned external to the body of the animal,
   measuring the temperature of the heater with the temperature sensor,
   generating heat with the heater at a rate sufficient to reduce a temperature gradient between the temperature transducer and the temperature sensor, and
   computing the internal body temperature of the animal using the temperature measurements from the temperature transducer and the temperature sensor.

10. The method of claim 9, wherein computing the internal body temperature further comprises:
   determining the temperature gradient between the temperature transducer and the temperature sensor,
   multiplying the temperature gradient by an experimentally determined constant.

11. A method of measuring an internal temperature of a human or other animal, comprising:
   applying external pressure to a compressible plug to compress and change the shape of the compressible plug,
   inserting the compressed plug into a body cavity of the animal such that a temperature transducer secured to an outside surface of the plug is positioned in thermal contact with the body cavity and a temperature sensor mounted on the outside surface of the plug is positioned external to the body cavity,
   allowing the compressed plug to expand and adapt to the shape of the body cavity so that the temperature transducer is in contact with a surface of the body cavity, and
   computing the internal temperature of the animal from temperature signals received from the temperature sensor and the temperature transducer.

* * * * *